United States Patent
Johns et al.

(10) Patent No.: US 10,772,889 B2
(45) Date of Patent: Sep. 15, 2020

(54) LIQUID NUTRITIONAL COMPOSITION CONTAINING 5-METHYLTETRAHYDROFOLIC ACID

(71) Applicant: Abbott Laboratories, Abbott Park, IL (US)

(72) Inventors: Paul Johns, Columbus, OH (US); Jeffrey Baxter, Westerville, OH (US); Megan Terp, Columbus, OH (US); Normanella Dewille, Columbus, OH (US); Youngsuk Heo, Powell, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 14 days.

(21) Appl. No.: 16/061,522

(22) PCT Filed: Dec. 19, 2016

(86) PCT No.: PCT/US2016/067528
§ 371 (c)(1),
(2) Date: Jun. 12, 2018

(87) PCT Pub. No.: WO2017/112588
PCT Pub. Date: Jun. 29, 2017

(65) Prior Publication Data
US 2019/0365761 A1   Dec. 5, 2019

Related U.S. Application Data

(60) Provisional application No. 62/270,096, filed on Dec. 21, 2015.

(51) Int. Cl.
| | | |
|---|---|---|
| *A61K 31/519* | (2006.01) | |
| *A23L 33/19* | (2016.01) | |
| *A23L 33/175* | (2016.01) | |
| *A23L 33/115* | (2016.01) | |
| *A23L 33/16* | (2016.01) | |
| *A23L 33/125* | (2016.01) | |
| *A23L 33/15* | (2016.01) | |
| *A23L 33/185* | (2016.01) | |
| *A23L 33/00* | (2016.01) | |
| *A61K 47/44* | (2017.01) | |

(52) U.S. Cl.
CPC .......... *A61K 31/519* (2013.01); *A23L 33/115* (2016.08); *A23L 33/125* (2016.08); *A23L 33/15* (2016.08); *A23L 33/16* (2016.08); *A23L 33/175* (2016.08); *A23L 33/185* (2016.08); *A23L 33/19* (2016.08); *A23L 33/40* (2016.08); *A61K 47/44* (2013.01); *A23V 2002/00* (2013.01)

(58) Field of Classification Search
CPC ............................. C07D 487/04; A61K 31/519
See application file for complete search history.

(56) References Cited

U.S. PATENT DOCUMENTS

2009/0239826 A1 * 9/2009 Halevie-Goldman ...................... A61K 31/198
514/89

FOREIGN PATENT DOCUMENTS

| ES | 2253089 A1 | 5/2006 |
|---|---|---|
| WO | 2006/119589 A2 | 11/2006 |

OTHER PUBLICATIONS

O'connor et al., American Family Physician, 2009, 79(7): 565570.*
Huang et al., Am J Clin Nutr, 2012, 95(5): 1048-54.*
Rzehak et al., Clin Nutr, 2011, 30(3): 339-45.*
Jain, Shreyansh et al., Development of Low Cost Nutritional Beverage from Whey, Journal of Environmental Science, Toxicology and Food Technology, vol. 1, Issue 1, pp. 73-88 (Jul.-Aug. 2013).
Liu Yazheng, Thermal Oxidation Studies on Reduced Folate, L-5-Methyltetrahydrofolic Acid (L-5-MTHF) and Strategies for Stabilization Using Food Matrices, Journal of Food Science, vol. 77, No. 2, pp. 236-243 (2012).
P H C J Verlinde et al., L-ascorbic acid improves the serum folate response to an oral dose of [6S]-5-methyltetrahydrofolic acid in healthy men, European Journal of Clinical Nutrition, vol. 62, No. 10. (2008).

* cited by examiner

*Primary Examiner* — Rei Tsang Shiao
(74) *Attorney, Agent, or Firm* — Porter Wright Morris & Arthur LLP

(57) ABSTRACT

A liquid nutritional composition including 5-methyltetrahydrofolic acid (5-MTHF) is provided. The liquid nutritional composition also includes ascorbic acid and a protein system containing methionine to inhibit or reduce oxidation of the 5-MTHF and provide an active folate level of the liquid nutritional composition that remains stable over the shelf life of the liquid nutritional composition.

20 Claims, No Drawings

LIQUID NUTRITIONAL COMPOSITION CONTAINING 5-METHYLTETRAHYDROFOLIC ACID

FIELD

The general inventive concepts relate to nutritional compositions. More particularly, the general inventive concepts relate to a liquid nutritional composition comprising 5-methyltetrahydrofolic acid (5-MTHF), wherein an active folate level of the liquid nutritional composition remains stable over the shelf life of the liquid nutritional composition.

BACKGROUND

Folate is an essential nutrient in humans and other animals. The human body uses folate to promote and restore cellular growth. Folate is especially important in aiding rapid cell division and growth, such as in infancy and pregnancy. Children and adults both require folate to produce healthy red blood cells and prevent anemia. In addition, low folate status has been associated with poor cognitive function.

Foods and supplements that are fortified with folate typically include the synthetic, oxidized folate compound folic acid due to its good stability under most food processing and storage conditions. In the human body, folic acid must be metabolized to provide a form of folate that is biologically active. One such biologically active folate is 5-MTHF, which is the predominant folate compound found in natural foods. Unlike folic acid, reduced folates such as 5-MTHF are generally susceptible to oxidation, which results in substantial losses when present in solution or when exposed to heat.

SUMMARY

The general inventive concepts relate to a liquid nutritional composition comprising 5-MTHF, wherein an active folate level of the liquid nutritional composition remains stable over the shelf life of the liquid nutritional composition. To illustrate various aspects of the general inventive concepts, several exemplary embodiments of liquid nutritional compositions are provided herein.

In one exemplary embodiment, a liquid nutritional composition is provided. The liquid nutritional composition includes a protein system comprising methionine, 5-MTHF or a salt thereof, and ascorbic acid or a salt thereof. A molar ratio of the methionine to the 5-MTHF is from 3,000:1 to 5,200:1.

In one exemplary embodiment, a molar ratio of the ascorbic acid to the 5-MTHF is from 1,800:1 to 30,000:1.

In one exemplary embodiment, the protein system includes a milk protein and a soy protein, and a weight ratio of the milk protein to the soy protein is from 80:20 to 50:50.

In one exemplary embodiment, the liquid nutritional composition includes the calcium salt of 5-MTHF.

In one exemplary embodiment, the liquid nutritional composition includes the sodium salt of ascorbic acid.

In one exemplary embodiment, a liquid nutritional composition is provided. The liquid nutritional composition includes a protein system that includes from 1.75% to 2.55% methionine by weight of the protein system, 5-MTHF or a salt thereof, and ascorbic acid or a salt thereof. A molar ratio of the methionine to the 5-MTHF is from 3,000:1 to 5,200:1.

DETAILED DESCRIPTION

While the general inventive concepts are susceptible of embodiment in many different forms, described herein in detail are specific embodiments thereof with the understanding that the present disclosure is to be considered as an exemplification of the principles of the general inventive concepts. Accordingly, the general inventive concepts are not intended to be limited to the specific embodiments illustrated and described herein.

The terminology set forth herein is for description of the embodiments only and should not be construed as limiting the disclosure as a whole. Unless otherwise specified, "a," "an," "the," and "at least one" are used interchangeably. Furthermore, as used in the description and the appended claims, the singular forms "a," "an," and "the" are inclusive of their plural forms, unless the context clearly indicates otherwise.

All percentages, parts, and ratios as used herein are by weight of the total composition, unless otherwise specified. All such weights as they pertain to listed ingredients are based on the active level and, therefore, do not include solvents or by-products that may be included in commercially available materials, unless otherwise specified.

The term "active folate level" as used herein, unless otherwise specified, refers to the concentration or amount of biologically active folates as determined by standard microbiological assays known in the art for determining folate content, or as determined by other suitable methods (now known or known in the future) for determining the concentration or amount of biologically active folates.

In one exemplary embodiment, a liquid nutritional composition is provided. The liquid nutritional composition comprises a protein system comprising methionine, 5-MTHF or a salt thereof, and ascorbic acid or a salt thereof. A molar ratio of the methionine to the 5-MTHF is from 3,000:1 to 5,200:1. The methionine present in the protein system, along with the ascorbic acid, function to inhibit or reduce the oxidative degradation of the 5-MTHF, which promotes a stable active folate level over the shelf life of the liquid nutritional composition. In one exemplary embodiment, the liquid nutritional composition is in the form of an aqueous emulsion having a continuous aqueous phase and a discontinuous non-aqueous phase.

The folate compound 5-MTHF is the predominant naturally occurring folate in foods. In the human body, 5-MTHF acts as an enzyme cofactor for transport of $C_1$ in methylation reactions in the biosynthesis of pyrimidines, purines, serine, and glycine. Fortification of foods and beverages with 5-MTHF has typically been avoided because 5-MTHF is particularly susceptible to oxidation, which can result in substantial losses of the 5-MTHF during processing and storage. In the exemplary liquid nutritional compositions described herein, it was discovered that the use of a protein system comprising methionine such that a molar ratio of the methionine to the 5-MTHF is from 3,000:1 to 5,200:1, along with ascorbic acid, can inhibit or reduce the loss of 5-MTHF and maintain a stable active folate level in the liquid nutritional composition over the shelf life of the liquid nutritional composition.

The exemplary liquid nutritional compositions described herein may be formulated with sufficient kinds and amounts of nutrients to provide a sole, primary, or supplemental source of nutrition, or may be formulated to provide a specialized liquid nutritional composition for use in individuals afflicted with specific diseases or conditions, or to provide a targeted nutritional benefit. The exemplary liquid nutritional compositions may be formulated as ready-to-feed or concentrated nutritional liquids.

In certain exemplary embodiments, the liquid nutritional composition is formulated as an emulsion. In certain exemplary embodiments, the liquid nutritional composition in emulsion form may be an aqueous emulsion comprising proteins, carbohydrates, and fats. Suitable emulsions for use herein are generally flowable or drinkable liquids at from 1° C. to 25° C., and are typically in the form of oil-in-water, water-in-oil, or complex aqueous emulsions, although such emulsions are most typically in the form of oil-in-water emulsions having a continuous aqueous phase and a discontinuous oil phase.

The exemplary liquid nutritional compositions described herein may be and typically are shelf stable. The nutritional liquids, typically contain up to 95% by weight of water, including from 50% to 95%, also including from 60% to 90%, and also including from 70% to 85% water by weight of the liquid nutritional composition. The exemplary liquid nutritional compositions described herein will generally have a shelf life of at least one year, and in some embodiments up to eighteen months.

The exemplary liquid nutritional compositions described herein may have a variety of product densities, but most typically have a density greater than 1.01 g/ml, including from 1.06 g/ml to 1.12 g/ml, and also including from 1.085 g/ml to 1.10 g/ml.

The exemplary liquid nutritional compositions described herein may have a pH ranging from 2.5 to 8, but are most advantageously in a range of from 4.5 to 7.5, including from 5.5 to 7.3, and including from 6.2 to 7.2.

As mentioned, the exemplary liquid nutritional compositions disclosed herein include 5-MTHF. The 5-MTHF utilized in the liquid nutritional compositions can be in free acid form or as a salt of 5-MTHF, or combinations thereof. Suitable salts of 5-MTHF include, but are not limited to, the calcium salt, the disodium salt, and the glucosamine salt. In one exemplary embodiment, the liquid nutritional composition comprises the calcium salt of 5-MTHF. The calcium salt of 5-MTHF is commercially available from Merck KGaA (Darmstadt, Germany).

In certain exemplary embodiments, the liquid nutritional composition comprises from 500 µg to 1,800 µg of 5-MTHF per liter of the liquid nutritional composition. For example, in certain exemplary embodiments, the liquid nutritional composition comprises from 500 µg to 1,750 µg of 5-MTHF per liter of the liquid nutritional composition, including from 550 µg to 1,750 from 600 µg to 1,725 from 750 µg to 1,690 from 850 µg to 1,565 from 1,055 µg to 1,480 or from 1,270 µs to 1,375 µg of 5-MTHF per liter of the liquid nutritional composition. In certain exemplary embodiments, the liquid nutritional composition comprises from 760 µg to 1,735 µg of 5-MTHF per liter of the liquid nutritional composition. In certain exemplary embodiments, the liquid nutritional composition comprises from 500 µg to 1,000 µg of 5-MTHF per liter of the liquid nutritional composition.

The exemplary liquid nutritional compositions described herein include a protein system comprising methionine. In one exemplary embodiment, the liquid nutritional composition comprises a protein system comprising from 1.75% to 2.55% methionine by weight of the protein system, including from 1.8% to 2.5%, from 1.9% to 2.4%, and also including from 2% to 2.55% methionine by weight of the protein system. The protein system may include one protein source or multiple (e.g., two, three, four) protein sources, provided that the protein system comprises an amount of methionine such that a molar ratio of the methionine to the 5-MTHF in the liquid nutritional composition is from 3,000:1 to 5,200:1. In certain exemplary embodiments, the molar ratio of the methionine to the 5-MTHF in the liquid nutritional composition is from 3,250:1 to 5,000:1, including from 3,500:1 to 4,750:1, from 3,750:1 to 4,500:1, or from 4,000:1 to 5,200:1. Without being bound by theory, it is believed that the particular range of molar ratios of the methionine to the 5-MTHF in the liquid nutritional composition provides protection against the oxidative degradation of 5-MTHF that would otherwise occur, thereby providing a stable active folate level over the shelf life of the liquid nutritional composition. In addition to being a constituent of the protein source, the methionine also functions as an antioxidant and protects the 5-MTHF against oxidation by reacting with reactive oxygen species that would otherwise react with and oxidize the 5-MTHF. While not wishing to be bound by theory, it is also believed that some, or most, of the 5-MTHF that undergoes oxidation is oxidized into other biologically active folate compounds, such as biologically active dihydrofolates.

The protein source or sources that comprise the protein system may be hydrolyzed, partially hydrolyzed, or non-hydrolyzed (i.e., intact) proteins, any of which can be derived from known or otherwise suitable sources such as milk (e.g., casein, milk protein isolate, milk protein concentrate, non-fat dry milk, whey), animal (e.g., meat, fish), cereal (e.g., rice, corn), vegetable (e.g., soy), legume (e.g., pea), or combinations thereof. Non-limiting examples of suitable proteins include milk protein concentrate, milk protein isolate, casein protein, whey protein isolate, whey protein concentrate, sodium caseinate, calcium caseinate, whole cow's milk, partially or completely defatted milk, soy protein isolates, soy protein concentrates, and so forth. The protein system, in certain embodiments, may comprise at least one free amino acid, non-limiting examples of which include methionine, tryptophan, glutamine, tyrosine, cysteine, arginine, and combinations thereof. The liquid nutritional compositions described herein can include any individual source of protein or combination of the various sources of protein listed above as the protein system, provided that the protein system comprises an amount of methionine such that a molar ratio of the methionine to the 5-MTHF in the liquid nutritional composition is from 3,000:1 to 5,200:1.

In certain exemplary embodiments, the liquid nutritional composition comprises from 0.5% to 20% protein by weight of the liquid nutritional composition. In certain exemplary embodiments, the liquid nutritional composition comprises from 1% to 15% protein by weight of the liquid nutritional composition, including from 2% to 10% protein by weight of the liquid nutritional composition, and also including from 3% to 6% protein by weight of the liquid nutritional composition. Alternatively, the protein present in the liquid nutritional composition may be expressed in terms of concentration. In certain exemplary embodiments, the liquid nutritional composition comprises from 20 grams to 85 grams of protein per liter of the liquid nutritional composition, including from 35 grams to 70 grams of protein per liter of the liquid nutritional composition, including from 40 grams to 55 grams of protein per liter of the liquid nutritional composition, and also including from 50 grams to 75 grams of protein per liter of the liquid nutritional composition.

In one exemplary embodiment, the liquid nutritional composition includes a protein system comprising a milk protein. In one exemplary embodiment, the liquid nutritional composition includes a protein system that comprises a milk protein and a soy protein, wherein a weight ratio of the milk protein to the soy protein is from 80:20 to 50:50, provided that the protein system comprises an amount of methionine such that the molar ratio of the methionine to the 5-MTHF in the liquid nutritional composition is from 3,000:1 to 5,200:1. Milk protein generally comprises from about 2 grams to about 2.5 grams of methionine per 100 grams of the milk protein, while soy protein generally comprises from about 1 gram to about 1.4 grams of methionine per 100 grams of the soy protein. In certain exemplary embodiments, the milk protein comprises a milk protein concentrate and the soy protein comprises a soy protein isolate. One suitable milk protein concentrate for use in the liquid nutritional compositions described herein is Alapro™ 4900, available from Fonterra (USA) Inc. (Rosemont, Ill., USA). One suitable soy protein isolate for use in the liquid nutritional compositions described herein is SUPRO® 1610, available from Solae, LLC (St. Louis, Mo., USA). In certain exemplary embodiments, the liquid nutritional composition includes a protein system that comprises a milk protein and a soy protein, and the weight ratio of the milk protein to the soy protein is from 75:25 to 55:45, including from 70:30 to 60:40, and also including from 80:20 to 65:35.

In one exemplary embodiment, the liquid nutritional composition includes a protein system such that a weight ratio of the protein provided by the protein system to the 5-MTHF is from 50,000:1 to 75,000:1, provided that the protein system also comprises an amount of methionine such that the molar ratio of the methionine to the 5-MTHF in the liquid nutritional composition is from 3,000:1 to 5,200:1. Without being bound by theory, it is believed that the particular range of weight ratios of the protein to the 5-MTHF provides protection to the 5-MTHF against oxidative degradation based on the ability of the protein to bind or otherwise interact with (e.g., through ion pairing) the 5-MTHF in the liquid nutritional composition. In certain exemplary embodiments, the liquid nutritional composition includes a protein system such that a weight ratio of the protein provided by the protein system to the 5-MTHF is from 55,000:1 to 75,000:1, including from 60,000:1 to 70,000:1, and also including from 65,000:1 to 75,000:1.

In one exemplary embodiment, the liquid nutritional composition includes a protein system comprising soluble protein such that a weight ratio of the soluble protein to the 5-MTHF is from 22,000:1 to 50,000:1, provided that the protein system also comprises an amount of methionine such that the molar ratio of the methionine to the 5-MTHF in the liquid nutritional composition is from 3,000:1 to 5,200:1. Without being bound by theory, it is believed that the particular range of weight ratios of the soluble protein to the 5-MTHF provides protection to the 5-MTHF against oxidation because the soluble protein is more available to react or otherwise interact with reactive oxygen species and prooxidant metals such as iron, which reduces the amount of reactive oxygen species and pro-oxidant metals that would otherwise oxidize the 5-MTHF in the liquid nutritional composition. In certain exemplary embodiments, the liquid nutritional composition includes a protein system comprising soluble protein such that a weight ratio of the soluble protein to the 5-MTHF is from 25,000:1 to 50,000:1, including from 30,000:1 to 45,000:1, from 35,000:1 to 40,000:1, and also including from 40,000:1 to 50,000:1.

The term "soluble protein" as used herein, unless otherwise specified, refers to those proteins having a protein solubility of at least about 40%, including from 50% to 100%, and also including from 60% to 90%, as measured in accordance with the following process: (1) suspend protein ingredient in purified water at 5.00 g per 100 g of suspension; (2) adjust the pH of the suspension to 6.8 or the desired product pH using NaOH, KOH, or HCl; (3) stir vigorously at room temperature (20° C. to 22° C.) for 60 minutes; (4) measure total protein in the suspension by any suitable technique (including the HPLC technique described below); (5) centrifuge an aliquot of the suspension at 31,000×g and at 20° C. for 1 hour; (6) measure the supernatant for protein by the selected technique as described in step (4); and (7) calculate protein solubility as the supernatant protein percentage of the total protein.

Protein concentration (per step 4 above) can be measured in the protein solubility process by any known or otherwise suitable method for determining such concentrations, many of which are well known in the analytical arts. An example of one such suitable method is by HPLC analysis in accordance with the following specifications: (1) Column: Shodex KW-804 protein size exclusion chromatography column, Waters P/N WAT036613; (2) Mobile Phase: 0.05M $NaH_2PO_4$, 0.15M NaCl, pH=7.0; (3) Flow Rate: 0.3 mL/minute; (4) Temperature: 22° C.; (5) Detection: UV at 214 nm; (6) Injection: 10 µL; (7) Run Time: 90 minutes; (8) System Calibration: protein standard solutions prepared at 0.5-3.0 g/L in mobile phase; and (9) Sample Preparation: dilute to about 1.5 g/L protein with mobile phase.

Any soluble protein source is suitable for use herein provided that it meets the solubility requirement as defined herein, and provided that the protein system comprises an amount of methionine such that the molar ratio of the methionine to the 5-MTHF in the liquid nutritional composition is from 3,000:1 to 5,200:1. Non-limiting examples of soluble proteins include whey protein concentrate (>90% solubility), whey protein isolate (>90% solubility), casein hydrolysate (>60% solubility), hydrolyzed collagen, and combinations thereof. In certain exemplary embodiments, the protein provided by the protein system comprises from 30% to 95% soluble protein by weight of the total protein in the liquid nutritional composition. In certain exemplary embodiments, the protein provided by the protein system comprises from 40% to 95% soluble protein by weight of the total protein in the liquid nutritional composition, including from 50% to 85% soluble protein by weight of the total protein in the liquid nutritional composition, and also including from 65% to 95% soluble protein by weight of the total protein in the liquid nutritional composition.

In addition to the protein system comprising methionine and the 5-MTHF or a salt thereof, the exemplary liquid nutritional compositions described herein comprise ascorbic acid or a salt of ascorbic acid. In certain exemplary embodiments, the liquid nutritional composition comprises ascorbic acid in free acid form. In certain exemplary embodiments, the liquid nutritional composition comprises a salt of ascorbic acid. In certain exemplary embodiments, the liquid nutritional compositions comprises ascorbic acid in free acid form, a salt of ascorbic acid, or both ascorbic acid in free acid form and a salt of ascorbic acid. Suitable salts of ascorbic acid for use in the liquid nutritional compositions described herein include, but are not limited to, sodium ascorbate, calcium ascorbate, potassium ascorbate, magnesium ascorbate, zinc ascorbate, molybdenum ascorbate, chromium ascorbate, and manganese ascorbate. In one exemplary embodiment, the liquid nutritional composition comprises the sodium salt of ascorbic acid (i.e., sodium ascorbate).

The ascorbic acid or ascorbate provides additional protection against the oxidative degradation of the 5-MTHF in the liquid nutritional composition. For example, the ascorbic acid or ascorbate functions as an antioxidant and protects the 5-MTHF against oxidation by reacting with reactive oxygen species that would otherwise react with and oxidize the 5-MTHF in the liquid nutritional composition. In certain exemplary embodiments, the liquid nutritional composition comprises an amount of ascorbic acid such that the molar ratio of the ascorbic acid to the 5-MTHF is from 1,800:1 to 30,000:1. In certain exemplary embodiments, the liquid nutritional composition comprises an amount of ascorbic acid such that the molar ratio of the ascorbic acid to the 5-MTHF is from 2,000:1 to 30,000:1, including from 5,000:1 to 25,000:1, from 10,000:1 to 20,000:1, and also including from 15,000:1 to 30,000:1.

In certain exemplary embodiments, in addition to the protein system, 5-MTHF or a salt thereof, and ascorbic acid or a salt thereof, the liquid nutritional composition comprises a carbohydrate, a fat, or both a carbohydrate and a fat.

In certain exemplary embodiments, the liquid nutritional composition comprises from 5% to 30% carbohydrate by weight of the liquid nutritional composition, including from 10% to 25% carbohydrate by weight of the liquid nutritional composition, from 15% to 20% carbohydrate by weight of the liquid nutritional composition, and also including from 18% to 30% carbohydrate by weight of the liquid nutritional composition. Alternatively, the amount of carbohydrate present in the liquid nutritional composition may be expressed in terms of concentration. In certain exemplary embodiments, the liquid nutritional composition comprises from 105 grams to 320 grams of carbohydrate per liter of the liquid nutritional composition, including from 145 grams to 275 grams of carbohydrate per liter of the liquid nutritional composition, including from 165 grams to 255 grams of carbohydrate per liter of the liquid nutritional composition, and also including from 190 grams to 235 grams of carbohydrate per liter of the liquid nutritional composition.

The carbohydrate or source of carbohydrate suitable for use in the liquid nutritional compositions disclosed herein may be simple, complex, or variations or combinations thereof. Generally, the carbohydrate may include any carbohydrate or carbohydrate source that is suitable for use in oral nutritional compositions and is otherwise compatible with any other selected ingredients or features in the liquid nutritional composition. Non-limiting examples of carbohydrates suitable for use in the liquid nutritional compositions described herein include, but are not limited to, maltodextrin; hydrolyzed or modified starch or cornstarch; polydextrose; glucose polymers; corn syrup; corn syrup solids; rice-derived carbohydrate; sucrose; glucose; fructose; lactose; high fructose corn syrup; honey; sugar alcohols (e.g., maltitol, erythritol, sorbitol); isomaltulose; sucromalt; pullulan; potato starch; and other slowly-digested carbohydrates; dietary fibers including, but not limited to, fructooligosaccharides (FOS), galactooligosaccharides (GOS), oat fiber, soy fiber, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinoglactins, glucomannan, xanthan gum, alginate, pectin, low methoxy pectin, high methoxy pectin, cereal beta-glucans (e.g., oat beta-glucan, barley beta-glucan), carrageenan, psyllium, and digestion resistant maltodextrin (e.g., Fibersol™, a digestion-resistant maltodextrin, comprising soluble dietary fiber); soluble and insoluble fibers derived from fruits or vegetables; other resistant starches; and combinations thereof. The liquid nutritional compositions described herein may include any individual source of carbohydrate or combination of the various sources of carbohydrate listed above.

In certain exemplary embodiments, the liquid nutritional composition comprises from 0.5% to 20% fat by weight of the liquid nutritional composition. In certain exemplary embodiments, the liquid nutritional composition comprises from 1% to 15% fat by weight of the liquid nutritional composition, including from 2% to 10% fat by weight of the liquid nutritional composition, and also including from 3% to 6% fat by weight of the liquid nutritional composition. Alternatively, the amount of fat present in the liquid nutritional composition may be expressed in terms of concentration. In certain exemplary embodiments, the liquid nutritional composition comprises from 20 grams to 85 grams of fat per liter of the liquid nutritional composition, including from 35 grams to 70 grams of fat per liter of the liquid nutritional composition, including from 40 grams to 55 grams of fat per liter of the liquid nutritional composition, and also including from 45 grams to 75 grams of fat per liter of the liquid nutritional composition.

The fat or source of fat suitable for use in the liquid nutritional compositions described herein may be derived from various sources including, but not limited to, plants, animals, and combinations thereof. Generally, the fat may include any fat or fat source that is suitable for use in oral nutritional compositions and is otherwise compatible with any other selected ingredients or features in the liquid nutritional composition. Non-limiting examples of suitable fat (or sources thereof) for use in the nutritional powders disclosed herein include coconut oil, fractionated coconut oil, soy oil, high oleic soy oil, corn oil, olive oil, safflower oil, high oleic safflower oil, medium chain triglyceride oil (MCT oil), high gamma linolenic (GLA) safflower oil, sunflower oil, high oleic sunflower oil, palm oil, palm kernel oil, palm olein, canola oil, high oleic canola oil, marine oils, fish oils, algal oils, borage oil, cottonseed oil, fungal oils, eicosapentaenoic acid (EPA), docosahexaenoic acid (DHA), arachidonic acid (ARA), conjugated linoleic acid (CLA), alpha-linolenic acid, rice bran oil, wheat bran oil, interesterified oils, transesterified oils, structured lipids, phospholipids (e.g., lecithin), and combinations thereof. These fats typically comprise triglycerides, although the fats may also comprise diglycerides, monoglycerides, and free fatty acids. Fatty acids provided by the fats in the nutritional powder include, but are not limited to, capric acid, lauric acid, myristic acid, palmitic acid, palmitoleic acid, stearic acid, oleic acid, linoleic acid, alpha-linolenic acid, ARA, EPA, and DHA. The liquid nutritional compositions described herein may include any individual source of fat or combination of the various sources of fat listed above.

The concentration and relative amounts of protein, carbohydrate, and fat in the exemplary liquid nutritional compositions can vary considerably depending upon, for example, the specific dietary needs of the intended user. In one exemplary embodiment, the liquid nutritional composition comprises protein in an amount of 2% to 15% by weight of the liquid nutritional composition, carbohydrate in an amount of 10% to 25% by weight of the liquid nutritional composition, and fat in an amount of 2% to 15% by weight of the liquid nutritional composition. In certain exemplary embodiments, the amount of protein, carbohydrate, and fat in the exemplary liquid nutritional composition may alternatively be expressed in terms of the percentage of total calories provided by the particular macronutrient, as shown below in Table 1.

TABLE 1

| Macronutrient | Embodiments | | |
| --- | --- | --- | --- |
| | A | B | C |
| Protein—% of total calories | 5-40 | 10-30 | 10-20 |
| Carbohydrate—% of total calories | 10-70 | 20-60 | 50-60 |
| Fat—% of total calories | 10-65 | 10-50 | 25-30 |

A serving of the liquid nutritional composition may vary widely depending on, for example, the nutritional needs of the intended user. For example, a serving of the liquid nutritional composition may be from 30 milliliters (mL) to 500 mL (~1 fl. oz. to ~17 fl. oz.). In certain exemplary embodiments, a serving of the liquid nutritional composition is from 110 mL to 500 mL (~3.7 fl. oz. to ~17 fl. oz.), including from 110 mL to 417 mL (~3.7 fl. oz. to ~14 fl. oz.), from 120 mL to 500 mL (~4 fl. oz. to ~17 fl. oz.), from 120 mL to 417 mL (~4 fl. oz. to ~14 fl. oz.), from 177 mL to 417 mL (~6 fl. oz. to ~14 fl. oz.), from 207 mL to 296 mL (~7 fl. oz. to ~10 fl. oz.), from 230 mL to 245 mL (~7.7 fl. oz. to ~8.2 fl. oz.), from 110 mL to 237 mL (~3.7 fl. oz. to ~8 fl. oz.), from 120 mL to 237 mL (~4 fl. oz. to ~8 fl. oz.), from 110 mL to 150 mL (~3.7 fl. oz. to ~5 fl. oz.), or from 120 mL to 150 mL (~4 fl. oz. to ~5 fl. oz.). Generally, as used herein, a serving may be construed as any amount which is intended to be consumed in one sitting or within one hour or less.

The liquid nutritional compositions, according to certain embodiments, may include optional components or ingredients that may modify the physical, chemical, aesthetic, or processing characteristics of the liquid nutritional composition or serve as a pharmaceutical or additional nutritional component. Many such optional ingredients are known or otherwise suitable for use in medical food or other nutritional products or pharmaceutical dosage forms and may also be used in the exemplary liquid nutritional compositions described herein, provided that such optional ingredients are safe for oral administration and are compatible with the essential and other ingredients described herein.

Non-limiting examples of such optional ingredients include vitamins, minerals, sweetening agents (e.g., high-intensity sweeteners), antioxidants, anti-foaming agents, preservatives, buffers, prebiotics, probiotics, pharmaceutical actives, anti-inflammatory agents, additional nutrients, colorants, flavors, thickening agents, stabilizers, emulsifying agents, and so forth.

In certain exemplary embodiments, the liquid nutritional composition may comprise any of a variety of vitamins or related nutrients, non-limiting examples of which include vitamin A, vitamin E, vitamin $D_2$, vitamin $D_3$, vitamin A palmitate, vitamin E acetate, vitamin C palmitate (ascorbyl palmitate), vitamin $K_1$, vitamin $K_2$, thiamine, riboflavin, pyridoxine, vitamin $B_{12}$, carotenoids (e.g., beta-carotene, zeaxanthin, lutein, lycopene), niacin, folic acid, pantothenic acid, biotin, choline, inositol, salts and derivatives of the foregoing, and combinations thereof. In certain exemplary embodiments, the liquid nutritional composition may comprise any of a variety of minerals, non-limiting examples of which include calcium, selenium, potassium, iodine, phosphorus, magnesium, iron, zinc, manganese, copper, sodium, molybdenum, chromium, chloride, and combinations thereof. In certain exemplary embodiments, the nutritional composition may comprise any combination of the foregoing vitamins and minerals.

In certain exemplary embodiments, the liquid nutritional composition may comprise a stabilizer. Any stabilizer that is known or otherwise suitable for use in a liquid nutritional composition is also suitable for use herein, some non-limiting examples of which include gums such as xanthan gum, guar gum, carrageenan, gum arabic, and so forth. In certain exemplary embodiments, the nutritional composition comprises from about 0.1 wt % to about 5 wt % of a stabilizer, including from about 0.5 wt % to about 3 wt %, or from about 0.7 wt % to about 1.5 wt % of a stabilizer.

The various embodiments of the exemplary liquid nutritional compositions described herein may be prepared by any process or suitable method (now known or known in the future) for making a liquid nutritional composition. Many such processes and methods are known for liquid nutritional compositions and can readily be applied by one of ordinary skill in the art to the various embodiments of the exemplary liquid nutritional compositions described herein.

In one suitable manufacturing process for preparing an emulsion-type liquid nutritional composition, for example, at least three separate slurries are prepared, including an oil slurry, a carbohydrate-mineral (CHO-MIN) slurry, and a protein-in-water (NW) slurry. The oil slurry may be formed by heating and mixing the fats and oils (e.g., soy oil, canola oil, corn oil) and adding any emulsifiers (e.g., lecithin, DATEM) and fat soluble vitamins with continued heat and agitation. The CHO-MIN slurry is formed by adding with heated agitation to water: minerals (e.g., potassium citrate, dipotassium phosphate, sodium citrate), including trace minerals, thickening or suspending agents (e.g., cellulose gel, gellan, carrageenan). The resulting CHO-MIN slurry is held for 10 minutes with continued heat and agitation before adding additional minerals (e.g., potassium chloride, magnesium carbonate, potassium iodide) and the carbohydrates (e.g., sucrose, corn syrup). The PIW slurry is then formed by mixing with heat and agitation the protein (e.g., milk protein concentrate, soy protein isolate) and water.

In accordance with this process, the three slurries are blended together with heat and agitation and the pH is adjusted to the desired range (e.g., from about 6.6 to about 7) after which the composition is subjected to high-temperature short-time ("HTST") processing. The composition is heat treated, emulsified, homogenized, and cooled during HTST. Water soluble vitamins, ultra trace minerals, and a vitamin C solution (with ascorbic acid or sodium ascorbate) containing the 5-MTHF are added, the pH is again adjusted (if necessary), flavors are added and any additional water can be added to adjust the solids content to the desired range. At this point, the liquid nutritional composition may optionally be packaged and sterilized according to any suitable sterilization technique (e.g., aseptic, retort, hot-fill, chemical, radiation, and filtering sterilization techniques).

The exemplary liquid nutritional compositions described herein contain 5-MTHF and the active folate level of the liquid nutritional compositions remains stable over the shelf life (e.g., one year) of the liquid nutritional compositions. In certain exemplary embodiments, the 5-MTHF or salt thereof is the sole source of folate used to formulate the liquid nutritional composition. As used herein with reference to "active folate level," the term "stable" refers to a subsequently tested active folate level that is at least 70% of an initially tested (or calculated) active folate level. For example, if a batch of a liquid nutritional composition is initially (e.g., on the day of production) tested (or calculated) and determined to have an active folate level of 500 then a subsequent test of a liquid nutritional composition from the same batch would need to have an active folate level of at least 350 µg to be considered "stable." The subsequent test is preferably conducted at a period of at least 6 months from the initial test, including 9 months from the initial test, 12 months from the initial test, 15 months from the initial test, and also including 18 months from the initial test. In certain exemplary embodiments, the liquid nutritional composition has a subsequent active folate level that is at least 75% of an initial active folate level, including at least 80%, at least 85%, at least 90%, or at least 95% of an initial active folate level. Thus, "stable" refers to such a maintenance of an active folate level over a period of time in which the liquid nutritional composition is intended to be usable (e.g., 9 months, 12 months, 15 months, 18 months).

EXAMPLES

The following examples illustrate certain exemplary embodiments of the liquid nutritional compositions and methods described herein. The examples are given solely for the purpose of illustration and are not to be construed as limitations of the general inventive concepts, as many variations thereof are possible without departing from the spirit and scope of the general inventive concepts.

Examples 1-3

Examples 1-3 illustrate exemplary liquid nutritional compositions in accordance with the general inventive concepts presented herein. The nutritional compositions of Examples 1-3 are in the form of an aqueous emulsion. All ingredient amounts in Examples 1-3 are listed in Table 2 as amount per 1000 kg batch of the liquid nutritional composition, unless otherwise indicated.

TABLE 2

| INGREDIENTS | Example 1 Amount per 1000 kg | Example 2 Amount per 1000 kg | Example 3 Amount per 1000 kg |
|---|---|---|---|
| Water | Q.S. kg | Q.S. kg | Q.S. kg |
| Milk Protein Concentrate | 41.2 kg | 41.2 kg | 41.2 kg |
| Maltodextrin | 22.2 kg | 20.3 kg | 20.3 kg |
| Canola oil | 16.2 kg | 16.1 kg | 16.1 kg |
| Sucrose | 14.4 kg | 13.2 kg | 13.2 kg |
| Soy Protein Isolate | 14.0 kg | 14.0 kg | 14.0 kg |
| Corn Oil | 5.4 kg | 5.4 kg | 5.4 kg |
| Magnesium Phosphate Dibasic | 3.2 kg | 6.9 kg | 6.9 kg |
| Cellulose Gel/Cellulose Gum Mixture | 3.0 kg | 3.0 kg | 3.0 kg |
| Potassium Citrate | 2.8 kg | 2.8 kg | 3.0 kg |
| Vanilla Flavor | 2.0 kg | 2.0 kg | 2.0 kg |
| Sodium Chloride | 1.2 kg | 1.2 kg | 1.2 kg |
| Soy Lecithin | 1.1 kg | 1.1 kg | 1.1 kg |
| Potassium Chloride | 759.8 g | 762.9 g | 762.9 g |
| Micronized-Tricalcium phosphate | 617.5 g | 618.4 g | 618.4 g |
| Calcium Carbonate | 535.4 g | 536.1 g | 536.1 g |
| Sodium Citrate | 492.8 g | 494.5 g | 222.8 g |
| Ascorbic Acid | 468.7 g | 567.8 g | |
| Sodium Ascorbate | | | 564.8 g |
| Mineral premix | 363.8 g | 363.8 g | 363.8 g |
| Iron | 17.9 g | 17.9 g | 17.9 g |
| Zinc | 15.5 g | 15.5 g | 15.5 g |
| Copper | 2.1 g | 2.1 g | 2.1 g |
| Manganese | 5.2 g | 5.2 g | 5.2 g |
| Selenium | 73.5 mg | 73.5 mg | 73.5 mg |
| Chromium | 99.7 mg | 99.7 mg | 99.7 mg |
| Molybdenum | 162.6 mg | 162.6 mg | 162.6 mg |
| 45% KOH | 323.2 g | 323.2 g | 323.2 g |
| Liquid Sucralose | 320.0 g | 330.7 g | 330.7 g |
| Carrageenan | 300.0 g | 300.0 g | 300.0 g |
| Lutein Powder (10%) | 257.8 g | | |
| Lutein Oil (20%) | | 152.1 g | 152.1 g |
| Acesulfame Potassium | 80.0 g | 88.2 g | 88.2 g |
| WSV Vitamin premix | 69.0 g | 69.0 g | 69.0 g |
| Niacinamide | 22.5 g | 22.5 g | 22.5 g |
| Pantothenic Acid | 13.4 g | 13.4 g | 13.4 g |
| Thiamine Hydrochloride | 3.7 g | 3.7 g | 3.7 g |
| Pyridoxine | 2.9 g | 2.9 g | 2.9 g |
| Riboflavin | 2.9 g | 2.9 g | 2.9 g |
| Folic Acid | 504.4 mg | 504.4 mg | 504.4 mg |
| Biotin | 438.2 mg | 438.2 mg | 438.2 mg |
| Cyanocobalamin | 9.5 mg | 9.5 mg | 9.5 mg |
| Vitamin DEK Premix | 65.3 g | 65.3 g | 65.3 g |
| Vitamin E | 34.5 g | 34.5 g | 34.5 g |
| Vitamin K1 | 73.2 mg | 73.2 mg | 73.2 mg |
| Vitamin D3 | 12.1 mg | 12.1 mg | 12.1 mg |
| Gellan Gum | 50.0 g | 50.0 g | 50.0 g |
| Vitamin A Palmitate, USP | 7.9 g | 7.9 g | 7.9 g |
| 5-MTHF Calcium Salt | 781.3 mg | 811.4 mg | 811.4 mg |
| Potassium Iodide | 207.2 mg | 207.2 mg | 207.2 mg |
| Methionine to 5-MTHF, molar ratio | 4,972:1 | 4,801:1 | 4,801:1 |
| Ascorbic Acid to 5-MTHF, molar ratio | 1,889:1 | 2,210:1 | 1,953:1 |
| Protein to 5-MTHF, w/w ratio | 72,601:1 | 69,896:1 | 69,896:1 |
| Soluble protein to 5-MTHF, w/w ratio | 39,931:1 | 38,443:1 | 38,443:1 |
| Methionine, g/100 g protein | 2.23 | 2.23 | 2.23 |

Example 4

This Example evaluates the active folate level of the liquid nutritional compositions of Examples 1, 2, and 3. Liquid nutritional compositions corresponding to Examples 1, 2, and 3 were formulated to have a total folate level (expressed as folic acid equivalents) of 1,350 µg per kg of the liquid nutritional composition. Accordingly, the initial active folate level of the liquid nutritional compositions was assumed to be 1,350 µg per kg of the liquid nutritional composition.

Sealed plastic bottles of the liquid nutritional compositions of Examples 1, 2, and 3 were stored for 9 months at room temperature. Samples of each liquid nutritional composition were tested for folate levels by two independent methods. One method utilized was a microbiological assay that determines the amount of all biologically active forms of folate present in a sample. A second method was used to determine the amount of folic acid and 5-MTHF present in a sample.

The amount of folic acid present in each sample was determined using a validated method (LC-MS/MS) for determining the folic acid concentration of nutritional products. Briefly, samples are prepared by protein precipitation with 1% acetic acid in methanol. Stable-isotope labeled internal standard—$^{13}C_5$-Folic Acid—is added to correct for sample preparation and instrument response variability. A series of working standard solutions spanning two orders of magnitude in folic acid concentration are used to generate calibration curves. Prepared samples and working standard solutions are injected onto an ultra-high pressure liquid chromatograph with a C-18 reverse phase column interfaced to a triple-quadrupole mass spectrometer (MS/MS) for analysis. The MS/MS is configured to monitor parent-daughter (precursor-fragment) ion pairs for folic acid and internal standard, calibrating response and assuring method selectivity. Quantitation is done by least squares regression using the peak response ratio of folic acid to the internal standard.

The amount of 5-MTHF present in each sample was determined by a method using reversed phase liquid chromatography separation (analytical LC column: Zorbax Elcipse Plus C18; 4.6×250 mm; 5 um; Agilent P/N 959990-902) with fluorescence detection (LC/FLD). The liquid nutritional product was prepared for 5-MTHF determination as follows: (a) a 1-gram sample was diluted to 10 mL with 0.05 M sodium citrate (4 mL) and acetonitrile (~5 mL); (b) the mixture was stirred vigorously for 2 minutes, and then allowed to stand until the protein precipitated (~15 minutes); (c) an aliquot (~4 mL) of the clear upper layer was filtered through a 0.45 um PTFE syringe filter; (d) 0.5 mL of the filtrate was diluted to 2 mL with 0.05 M sodium citrate; and (e) a 2 uL volume of the diluted filtrate was immediately injected into the LC system. The results of each method are shown below in Table 3, with the values represented as µg of folic acid equivalents per kg of sample.

TABLE 3

| Sample | Total Folates by Microbiological Assay (µg/kg sample) | Folic Acid by LC-MS/MS (µg/kg sample) | 5-MTHF by LC/FLD (µg/kg sample) | % of Total Folate[1] in Sample | % of Total Folate[2] in Sample |
|---|---|---|---|---|---|
| Example 1 | 1,297 | 530 | 455 | 96 | 73 |
| Example 2 | 1,207 | 530 | 433 | 89 | 71 |
| Example 3 | 1,213 | 545 | 477 | 90 | 76 |

[1]Calculated as (Total Folates by Microbiological Assay/1,350)*100.
[2]Calculated as ((Folic Acid + 5-MTHF)/1,350)*100.

As the data of Table 3 demonstrates, the amount of total folates in the liquid nutritional compositions of Examples 1, 2, and 3 remained stable over a 9 month shelf life by retaining at least 89% of the active folate level as determined by microbiological assay. When using the second test method that only determined the amount of folic acid and 5-MTHF, the percentage of total folate in each sample was lower than the percentage of total folate determined by microbiological assay. Since the individual samples tested by each method were from the same individual batches, a comparison of the results of each method indicate that biologically active folates other than folic acid and 5-MTHF were present in each sample tested. Without being bound by theory, it is believed that a portion of the 5-MTHF in the samples is converted via an oxidation reaction to other biologically active folates, such as dihydrofolates. Accordingly, this Example demonstrates that the use of 5-MTHF in a liquid nutritional composition can have an active folate level that remains stable over the shelf life of the liquid nutritional composition.

The various embodiments of the liquid nutritional compositions of the present disclosure may also be substantially free of any optional or selected essential ingredient or feature described herein, provided that the remaining liquid nutritional composition still contains all of the required ingredients or features as described herein. In this context, and unless otherwise specified, the term "substantially free" means that the selected nutritional composition contains less than a functional amount of the optional ingredient, typically less than about 1%, including less than about 0.5%, including less than about 0.1%, and also including zero percent, by weight of such optional or selected essential ingredient.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

The liquid nutritional compositions may comprise, consist of, or consist essentially of the essential elements of the compositions as described herein, as well as any additional or optional element described herein or otherwise useful in nutritional composition applications.

Although the present disclosure has been described with reference to specific embodiments, it should be understood that the limitations of the described embodiments are provided merely for purpose of illustration and are not intended to limit the present invention and associated general inventive concepts. Instead, the scope of the present invention is defined by the appended claims, and all variations and equivalents that fall within the range of the claims are intended to be embraced therein. Thus, other embodiments than the specific exemplary ones described herein are equally possible within the scope of the appended claims.

What is claimed is:

1. A liquid nutritional composition comprising:
    a protein system comprising methionine;
    5-methyltetrahydrofolic acid or a salt thereof; and
    ascorbic acid or a salt thereof;

wherein a molar ratio of the methionine to the 5-methyltetrahydrofolic acid is from 3,000:1 to 5,200:1.

2. The liquid nutritional composition according to claim 1, wherein a molar ratio of the ascorbic acid to the 5-methyltetrahydrofolic acid is from 1,800:1 to 30,000:1.

3. The liquid nutritional composition according to claim 1, wherein the protein system comprises a milk protein and a soy protein, and wherein a weight ratio of the milk protein to the soy protein is from 80:20 to 50:50.

4. The liquid nutritional composition according to claim 1, wherein a weight ratio of the protein system to the 5-methyltetrahydrofolic acid is from 50,000:1 to 75,000:1.

5. The liquid nutritional composition according to claim 1, wherein the protein system comprises soluble protein, and wherein a weight ratio of the soluble protein to the 5-methyltetrahydrofolic acid is from 22,000:1 to 50,000:1.

6. The liquid nutritional composition according to claim 1, wherein the liquid nutritional composition comprises the calcium salt of 5-methyltetrahydrofolic acid.

7. The liquid nutritional composition according to claim 1, wherein the liquid nutritional composition comprises the sodium salt of ascorbic acid.

8. The liquid nutritional composition according to claim 1, further comprising a carbohydrate and a fat.

9. The liquid nutritional composition according to claim 8, wherein the carbohydrate comprises at least one of sucrose, lactose, fructose, glucose, corn syrup, maltodextrin, fructooligosaccharides, galactooligosaccharides, cornstarch, polydextrose, starch, and a sugar alcohol.

10. The liquid nutritional composition according to claim 8, wherein the fat comprises at least one of canola oil, corn oil, coconut oil, fractionated coconut oil, soy oil, high oleic soy oil, olive oil, safflower oil, high oleic safflower oil, high gamma-linolenic acid safflower oil, medium chain triglyceride oil, sunflower oil, high oleic sunflower oil, palm oil, palm kernel oil, palm olein, high oleic canola oil, marine oil, cottonseed oil, eicosapentaenoic acid, docosahexaenoic acid, gamma-linolenic acid, rice bran oil, wheat germ oil, algal oil, nut oil, fungal oil, and conjugated linolenic acid.

11. A liquid nutritional composition comprising:
a protein system comprising from 1.75% to 2.55% methionine by weight of the protein system;
5-methyltetrahydrofolic acid or a salt thereof; and
ascorbic acid or a salt thereof;
wherein a molar ratio of the methionine to the 5-methyltetrahydrofolic acid is from 3,000:1 to 5,200:1.

12. The liquid nutritional composition according to claim 11, wherein a molar ratio of the ascorbic acid to the 5-methyltetrahydrofolic acid is from 1,800:1 to 30,000:1.

13. The liquid nutritional composition according to claim 11, wherein the protein system comprises a milk protein.

14. The liquid nutritional composition according to claim 13, wherein the protein system further comprises a soy protein, and wherein a weight ratio of the milk protein to the soy protein is from 80:20 to 50:50.

15. The liquid nutritional composition according to claim 11, wherein a weight ratio of the protein system to the 5-methyltetrahydrofolic acid is from 50,000:1 to 75,000:1.

16. The liquid nutritional composition according to claim 11, wherein the liquid nutritional composition comprises the calcium salt of 5-methyltetrahydrofolic acid.

17. The liquid nutritional composition according to claim 11, wherein the liquid nutritional composition comprises the sodium salt of ascorbic acid.

18. The liquid nutritional composition according to claim 11, further comprising a carbohydrate and a fat.

19. The liquid nutritional composition according to claim 18, wherein the carbohydrate comprises at least one of sucrose, lactose, fructose, glucose, corn syrup, maltodextrin, fructooligosaccharides, galactooligosaccharides, cornstarch, starch, polydextrose, and a sugar alcohol.

20. The liquid nutritional composition according to claim 18, wherein the fat comprises at least one of canola oil, corn oil, coconut oil, fractionated coconut oil, soy oil, high oleic soy oil, olive oil, safflower oil, high oleic safflower oil, high gamma-linolenic acid safflower oil, medium chain triglyceride oil, sunflower oil, high oleic sunflower oil, palm oil, palm kernel oil, palm olein, high oleic canola oil, marine oil, cottonseed oil, eicosapentaenoic acid, docosahexaenoic acid, gamma-linolenic acid, rice bran oil, wheat germ oil, algal oil, nut oil, fungal oil, and conjugated linolenic acid.

* * * * *